United States Patent [19]
Liotta, Jr. et al.

[11] Patent Number: 5,312,998
[45] Date of Patent: May 17, 1994

[54] INTEGRATED PROCESS FOR THE PRODUCTION OF DITERTIARY BUTYL PEROXIDE

[75] Inventors: Frank J. Liotta, Jr., Collegeville; Mahmoud K. Faraj, Newtown Square; Daniel B. Pourreau, Downingtown; Haven S. Kesling, Jr., Drexel Hill, all of Pa.

[73] Assignee: Arco Chemical Technology, L.P., Wilmington, Del.

[21] Appl. No.: 75,185

[22] Filed: Jun. 10, 1993

[51] Int. Cl.$^5$ .................................. C07C 409/16
[52] U.S. Cl. .......................... 568/578; 568/558
[58] Field of Search ......................... 568/578, 558

[56] References Cited
U.S. PATENT DOCUMENTS

| | | | |
|---|---|---|---|
| 2,383,919 | 8/1945 | Rust et al. | 568/578 |
| 2,403,771 | 7/1946 | Vaughan et al. | 568/561 |
| 2,862,973 | 12/1958 | Winkler et al. | 568/578 |
| 3,833,664 | 9/1974 | Aoshima | 568/578 |
| 4,198,528 | 4/1980 | Kelsey | 568/578 |
| 4,266,081 | 5/1981 | Mizuno et al. | 568/578 |
| 4,810,809 | 3/1989 | Sanderson et al. | 568/562 |
| 4,900,850 | 2/1990 | Sanderson et al. | 568/578 |

Primary Examiner—Werren B. Lone
Attorney, Agent, or Firm—John C. Martin, Jr.

[57] ABSTRACT

An integrate process is provided for the production of ditertiary butyl peroxide wherein isobutane oxidate containing tertiary butyl alcohol and tertiary butyl hydroperoxide is reacted in the presence of an aqueous acidic catalyst, the reaction mixture is phase separated, the aqueous catalyst is recovered and recycled, and the product peroxide is recovered from the organic phase by water extraction.

4 Claims, 1 Drawing Sheet

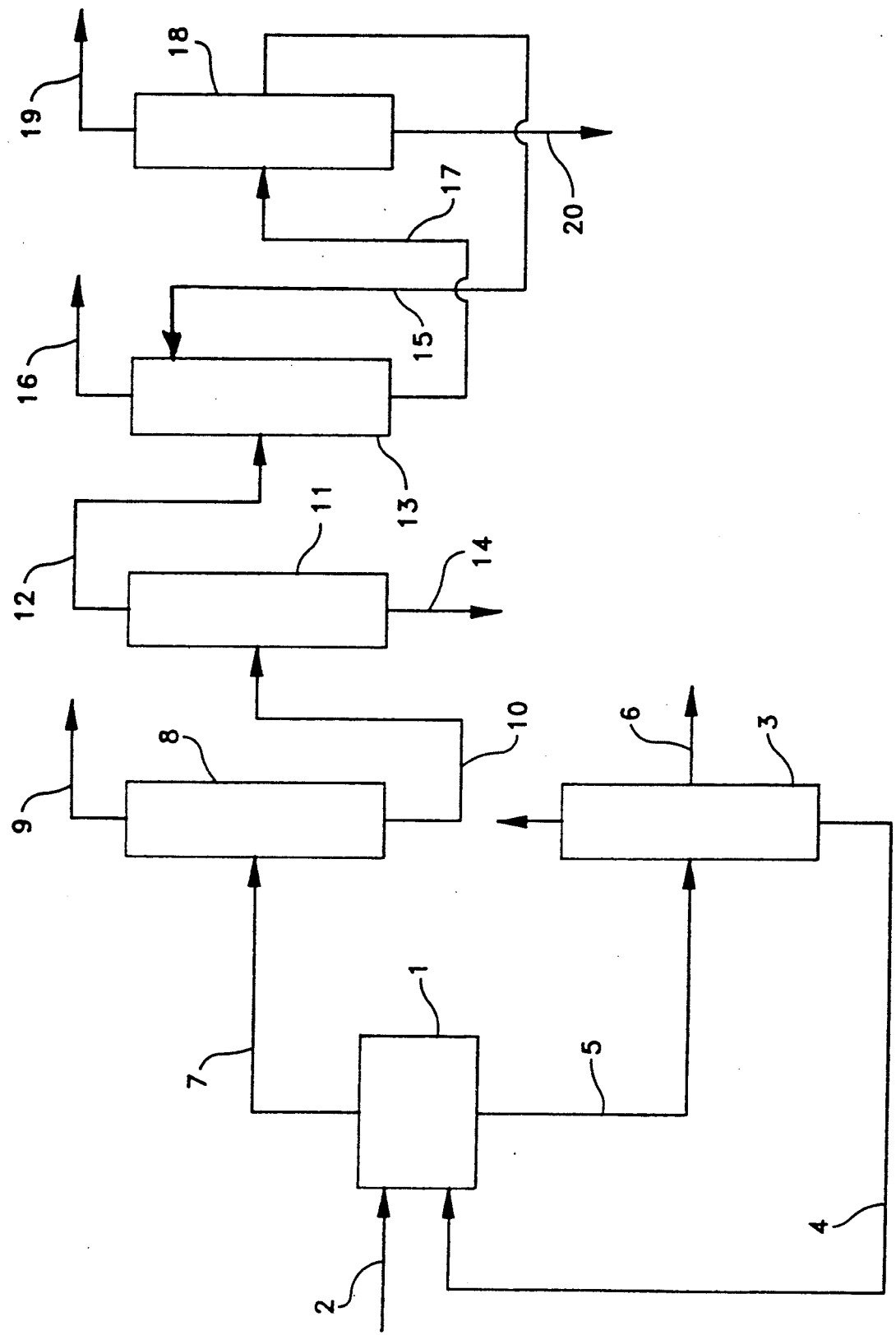

INTEGRATED PROCESS FOR THE PRODUCTION OF DITERTIARY BUTYL PEROXIDE

BACKGROUND OF THE INVENTION

1. Field of the Invention

The present invention provides an integrated process for the production of ditertiary butyl peroxide from isobutane oxidate wherein the oxidate containing tertiary butyl alcohol and tertiary butyl hydroperoxide is reacted in the presence of a water soluble acid catalyst, the reaction mixture is resolved into separate aqueous and organic phases, tertiary butyl alcohol is recovered from the aqueous phase and the water soluble catalyst is recycled, and the organic phase is resolved in order to recover product ditertiary butyl peroxide.

2. Description of the Prior Art

The production of ditertiary butyl peroxide by reaction of the tertiary butyl alcohol and tertiary butyl hydroperoxide components of an isobutane reaction mixture is known. See, for example, U.S. Pat. No. 2,862,973.

The recovery of ditertiary butyl peroxide from admixtures containing tertiary butyl hydroperoxide and tertiary butyl alcohol is likewise known. See, for example, U.S. Pat. No. 2,383,919. A later patent which seems to cover much the same subject matter is U.S. Pat. No. 4,900,850.

Ditertiary butyl peroxide is an important chemical having use for example as a catalyst in various organic syntheses but having special utility as an additive to diesel fuel formulations in order to improve the characteristics thereof. Although methods have been suggested for the production and recovery of ditertiary butyl peroxide, as above indicated, there remains considerable room for improvement in the efficiency and economics of the technology for producing this product.

SUMMARY OF THE INVENTION

In accordance with the invention, isobutane oxidate comprised of both tertiary butyl alcohol and tertiary butyl hydroperoxide is reacted in the presence of a water soluble acid catalyst under conditions effective to form ditertiary butyl peroxide. The reaction mixture is phase separated in order to separately recover an aqueous phase containing tertiary butyl alcohol and the acid catalyst and an organic phase containing ditertiary butyl peroxide. The aqueous phase is distilled in order to recover tertiary butyl alcohol overhead and also to separate any water produced during the reaction or introduced in the reaction feed streams, and a concentrated aqueous acid stream is recovered and recycled to the peroxide-forming reaction. The organic phase containing product ditertiary butyl peroxide is then subjected to a series of separation steps including a water extraction step in order to recover product ditertiary butyl peroxide as well as such tertiary butyl alcohol as is contained in the organic phase.

BRIEF DESCRIPTION OF THE DRAWING

The attached drawing illustrates in schematic form practice of the invention.

DETAILED DESCRIPTION OF THE INVENTION

In accordance with the invention, isobutane is reacted with molecular oxygen in accordance with known procedures to produce a mixture containing both tertiary butyl alcohol and tertiary butyl hydroperoxide. Suitable conditions for carrying out this oxidation are shown, for example, in U.S. Pat. No. 2,862,973. In accordance with the invention, the mixture of tertiary butyl alcohol and tertiary butyl hydroperoxide is then reacted in accordance with known procedures in the presence of water soluble acid catalyst in order to form product ditertiary butyl peroxide. Suitable catalysts for carrying out this reaction include sulfonic acid, inorganic heteropoly acids, methane sulfonic acid, toluene sulfonic acid and other water soluble protic and Lewis acids. Copending application Ser No. 08/061,139 filed May 13, 1993 describes peroxide formation using inorganic heteropoly acid catalysts. The reaction is carried out in accordance with known procedures as a two-phase reaction mixture. Generally, temperatures in the range of about 70° to 110° C. are suitable, but this can vary quite widely.

Upon completion of the desired reaction between tertiary butyl alcohol and tertiary butyl hydroperoxide, the two-phase reaction mixture is resolved into separate aqueous and organic phases. The aqueous phase contains water, the water soluble acid catalyst and certain amounts of tertiary butyl alcohol and other water soluble materials. The organic phase contains the product ditertiary butyl peroxide, tertiary butyl alcohol, any unreacted tertiary butyl hydroperoxide and other components.

In accordance with the invention, it is essential that the acid catalyst be recovered from the aqueous phase and recycled to the peroxide-forming reaction zone. This is accomplished by phase separating the reaction mixture, passing the aqueous phase to a distillation zone wherein a tertiary butyl alcohol/water azeotrope and any excess water is separated overhead and a concentrated aqueous solution of the acid catalyst is recovered as a bottoms stream and recycled to the peroxide-forming reaction zone. Water of reaction and water introduced with various reagents can be removed as an intermediate stream from this distillation.

The organic phase recovered from the peroxide-forming reaction comprises tertiary butyl alcohol and ditertiary butyl peroxide and may contain substantial amounts of tertiary butyl hydroperoxide. Suitably, this organic phase is first subjected to a distillation in order to recover overhead any isobutylene which may be present and which can be, if desired, recycled to the peroxide-forming reaction.

The bottoms from this distillation is then treated in order to accomplish the recovery of the product ditertiary butyl peroxide. Depending upon the amount of unreacted tertiary butyl hydroperoxide in the mixture, this separation may be accomplished in one of two ways. If there is substantial unreacted hydroperoxide in the organic phase, it is advantageous to subject this organic phase to a distillation with the removal overhead of a low-boiling azeotrope comprised of ditertiary butyl peroxide and tertiary butyl alcohol. In this procedure, the bottoms which is concentrated in the hydroperoxide can be recovered and recycled to the peroxide-forming reaction zone.

The low-boiling azeotrope of tertiary butyl alcohol and ditertiary butyl peroxide can be conveniently separated by a water extraction procedure whereby the tertiary butyl alcohol is water extracted away from the product ditertiary butyl peroxide. Similarly, where the organic phase from the peroxide-forming reaction zone contains very little hydroperoxide, e.g. less than about 2% by weight, the above azeotropic distillation is not necessary and the organic phase itself can be directly subjected to water extraction for the separation of product ditertiary butyl peroxide from the tertiary butyl alcohol.

In either of the above procedures, the aqueous extract comprised primarily of water and tertiary butyl alcohol, can be distilled in a conventional fashion in order to separate tertiary butyl alcohol from the water extraction stream, the latter being conveniently recycled for further extraction use.

Any remaining traces of hydroperoxide in the product ditertiary butyl peroxide can be effectively separated by extraction with an aqueous solution of hydroxide or bisulfite or by passing the peroxide through a bed of alumina.

As above described, the process of the invention is represented by an integrated sequence of integrated steps whereby ditertiary butyl peroxide is produced and recovered with high efficiency and at minimum cost.

The invention can be further described in connection with the accompanying drawing. Referring to the drawing, a debutanized isobutane oxidate containing tertiary butyl hydroperoxide and tertiary butyl alcohol is introduced into reaction/separation zone 1 via line 2. In zone 1 the oxidate is contacted at reactive conditions with an aqueous acid catalyst stream which is recycled from distillation zone 3 via line 4.

In zone 1 tertiary butyl hydroperoxide is catalytically reacted with tertiary butyl alcohol to form ditertiary butyl peroxide. Isobutylene can be added to the reaction mixture (not shown), and it is generally advantageous to use a substantial excess of tertiary butanol and/or isobutylene relative to the hydroperoxide and carry out the reaction for a sufficient time to achieve high hydroperoxide conversion, e.g. 90% or more. A plurality of reaction zones can be employed in series to facilitate high hydroperoxide conversion.

The reaction mixture is separated in zone 1 by conventional procedures into an organic phase comprised predominantly of product ditertiary butyl peroxide and tertiary butanol and an aqueous phase predominantly comprised of water, acid catalyst and tertiary butanol.

The aqueous catalyst-containing phase is passed via line 5 to distillation zone 3 wherein the catalyst is concentrated and purified for recycle. The aqueous phase from zone 1 is distilled in zone 3 to separate an aqueous tertiary butanol azeotrope overhead which can be processed in a conventional fashion for the recovery of tertiary butanol values. Net water produced by the peroxide-forming reaction as well as that introduced with the isobutane oxidate is separated from zone 3 via line 6 and the concentrated aqueous acid catalyst stream passes via line 4 back to reaction zone 1 for further use in the peroxide production.

The organic phase from zone 1 is comprised of ditertiary butyl peroxide and tertiary butanol. The organic phase passes via line 7 to distillation zone 8 wherein isobutylene which is formed by tertiary butanol dehydration and/or which is added as a reactant to zone 1 is separated overhead via line 9. A bottoms stream comprised of product peroxide and tertiary butanol passes from zone 8 via line 10 for peroxide recovery.

In general, the separation of product ditertiary butyl peroxide from tertiary butanol is accomplished by water extraction. However, in the case where a substantial percentage of the organics from zone 1 comprises unreacted hydroperoxide, it is advantageous first to distill a low-boiling tertiary butanol/ditertiary butyl peroxide or tertiary butanol/ditertiary butyl peroxide/water azeotrope overhead from a tertiary butyl hydroperoxide and tertiary butyl alcohol fraction. As illustrated in the drawing, the bottoms from zone 8 containing substantial hydroperoxide passes via line 10 to distillation zone 11. The low-boiling tertiary butyl peroxide/tertiary butanol azeotrope passes overhead via line 12 from zone 11 to water extraction zone 13. A bottoms stream comprised of tertiary butyl hydroperoxide and tertiary butanol is removed via line 14 and this stream can be recycled to reaction zone 1.

In the case where there is substantially complete hydroperoxide conversion in zone 1, the distillation in zone 11 can be omitted and the bottoms from zone 8 passed directly to water extraction separation in zone 13.

In zone 13, the organic mixture comprised mainly of product peroxide and tertiary butanol is resolved by water extraction. Water is introduced into zone 13 via line 15 and extracts tertiary butanol from the product ditertiary butyl peroxide which is recovered via line 16. The aqueous extract stream passes from zone 13 via line 17 to distillation zone 18 where the tertiary butanol is distilled overhead along with some water via line 19 while the extraction water is recycled via line 15 to zone 13. The aqueous tertiary butanol stream removed via line 19 can be further treated by conventional means for tertiary butanol recovery.

The practice of the invention can be more fully illustrated by the following example:

EXAMPLE

Referring to the accompanying drawing, isobutane oxidate in the amount of 10 lbs./hr. is introduced into reaction zone 1 via line 2. This oxidate comprises by weight 40% tertiary butyl hydroperoxide and 56% tertiary butyl alcohol. Also introduced into zone 1 via line 4 at the rate of 1.94 lbs./hr. is an aqueous acid catalyst comprised by weight of 50% water and 50% phosphotungstic acid. Conditions in zone 1 are maintained at a temperature of 85° C., and the system pressure is 80 psig.

The reaction mixture is phase separated and an aqueous phase containing the catalyst is removed via line 5 at the rate of 2.7 lbs./hr. and passed to distillation column 3. In column 3 an overhead mixture of tertiary butyl alcohol and water comprised of 87% by weight tertiary butyl alcohol is separated at the rate of 0.85 lbs./hr. The overhead conditions are 80° C. and atmospheric pressure. An intermediate sidestream comprised of excess water is removed via line 6 at the rate of 0.78 lbs./hr. The bottoms aqueous acid stream is removed via line 4 and recycled to reactor 1.

The organic phase, comprised of product ditertiary butyl peroxide, is separated at the rate of 7.75 lbs./hr. via line 7. This stream comprises by weight 74% peroxide, 1.9% tertiary butyl hydroperoxide and 18.7% tertiary butyl alcohol and 3.7% isobutylene. The organic stream passes via line 7 to distillation column 8 wherein isobutylene is separated overhead via line 9 at the rate of 0.29 lbs./hr.; conditions at the top of column 8 are 55° C. and 100 psia.

From column 7 the bottoms stream is separated via line 10 at the rate of 7.5 lbs./hr. The composition of this bottoms by weight is 77% peroxide, 19% tertiary butyl alcohol and 1.9% tertiary butyl hydroperoxide. Stream 10 passes directly to water extraction zone 13 wherein tertiary butyl alcohol is separated from the product ditertiary butyl peroxide by water extraction. Note that in view of the small concentration of tertiary butyl hydroperoxide in stream 10, it is not necessary that the mixture be distilled in column 11 as indicated on the attached drawing.

In extraction zone 13 water is added via line 15 at the rate of 15 lbs./hr. An upper organic stream comprised of product peroxide is removed via line 16 at the rate of 6.0 lbs./hr. The purity of the ditertiary butyl peroxide product is 95 wt. %.

An aqueous stream containing the tertiary butyl alcohol is removed from zone 13 via line 17 at the rate of 16.5 lbs./hr. The composition of this stream by weight is 7% tertiary butyl alcohol and 91% water. The stream passes via line 17 to distillation column 18, and a tertiary butyl alcohol/water mixture is distilled overhead at 80° C. and atmospheric pressure at the rate of 16 lbs./hr. This stream has the composition by weight 87% tertiary butyl alcohol and 13% water.

An aqueous stream is withdrawn and recycled via line 15 to extraction zone 13 as above indicated. The purge stream in the amount of 0.8 lbs./hr. is separated via line 20.

I claim:

1. A process for the production of ditertiary butyl peroxide which comprises reacting isobutane oxidate containing tertiary butyl hydroperoxide and tertiary butyl alcohol in the presence of a water soluble protic or Lewis acid catalyst, separating the reaction product mixture into an organic ditertiary butyl peroxide-containing phase and an aqueous phase containing tertiary butyl alcohol and the said catalyst, distilling the aqueous phase in order to separate tertiary butyl alcohol and the said catalyst and recycling the aqueous solution of said catalyst to the peroxide reaction zone, water extracting tertiary butyl alcohol from teriary butyl peroxide in the said organic phase and recovering the tertiary butyl peroxide product.

2. The process of claim 1 wherein the water soluble catalyst is an inorganic heteropoly acid.

3. The process of claim 1 wherein the water soluble catalyst is phosphotungstic acid.

4. A process for the production of ditertiary butyl peroxide which comprises reacting isobutane oxidate containing tertiary butyl hydroperoxide and tertiary butyl alcohol in the presence of a water soluble protic or Lewis acid catalyst, separating the reaction product mixture into an organic ditertiary butyl peroxide-containing phase and an aqueous phase containing tertiary butyl alcohol and the said catalyst, distilling the aqueous phase in order to separate tertiary butyl alcohol from an aqueous solution of said catalyst and recycling the aqueous solution of said catalyst to the peroxide reaction zone, distilling the organic ditertiary butyl peroxide-containing phase and separating an overhead diteritiary butyl peroxide and tertiary butyl alcohol stream, water extracting butyl alcohol from tertiary butyl peroxide in the said overhead stream and recovering the tertiary butyl peroxide product.

* * * * *